United States Patent [19]

Kast et al.

[11] Patent Number: 4,842,638
[45] Date of Patent: Jun. 27, 1989

[54] HERBICIDAL TETRAHYDRO(THIO)PYRAN-2,4-DIONE DERIVATIVES

[75] Inventors: Juergen Kast, Boehl-Iggelheim; Michael Keil, Freinsheim; Dieter Kolassa, Ludwigshafen; Ulrich Schirmer, Heidelberg; Bruno Wuerzer, Otterstadt; Norbert Meyer, Ladenburg; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 142,911

[22] Filed: Jan. 12, 1988

[51] Int. Cl.4 .................. A01N 43/16; A01N 43/18; C07D 407/04; C07D 409/04
[52] U.S. Cl. ........................... 71/88; 71/90; 549/13; 549/28; 549/60; 549/377; 549/414; 549/415
[58] Field of Search ............... 549/28, 13, 60, 377, 549/414, 415; 71/89, 90, 88

[56] References Cited

PUBLICATIONS

Shandala et al., *J. Heterocyclic Chem.* 21, 1755 (1984).
Seebach & Meyer, *Angew. Chem.* 86, 40 (1974).

*Primary Examiner*—Mary C. Lee
*Assistant Examiner*—MarySue Howard
*Attorney, Agent, or Firm*—Keil & Weinkauf

[57] ABSTRACT

Tetrahydro(thio)pyran-2,4-dione derivatives of the formula

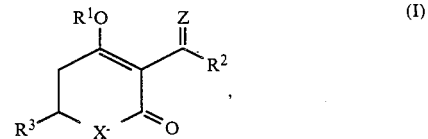

where $R^1$ is hydrogen, a cation, alkylcarbonyl, $C_2$–$C_{10}$-alkenylcarbonyl, or benzoyl which is unsubstituted or substituted by alkyl, $R^2$ is alkyl, $R^3$ is a non-aromatic, unsubstituted or alkyl-substituted heterocyclic compound of 5 to 7 ring members and having at most one double bond in the heterocyclic ring, X is oxygen or sulfur, and Z is oxygen or the radical NO—$R^4$, $R^4$ denoting alkyl, alkenyl, alkynyl, haloalkyl, haloalkenyl, alkoxyalkyl or the radical $CH_2$—$R^5$, where $R^5$ is a heterocyclic compound of 5 ring members and containing from 1 to 3 hetero-atoms and from 0 to 2 double bonds and bearing either no substituents or one or two substituents selected from the group consisting of alkyl, alkoxy, halogen, trifluoromethyl, alkoxymethyl, alkylthiomethyl and vinyl, or $R^5$ is phenyl which is unsubstituted or bears from one to three substituents selected from the group consisting of alkyl, alkoxy, halogen, trifluoromethyl, nitro and dialkylamino, and their use for combating unwanted plant growth and for regulating plant growth.

7 Claims, No Drawings

HERBICIDAL TETRAHYDRO(THIO)PYRAN-2,4-DIONE DERIVATIVES

The present invention relates to novel tetrahydro(thio)pyran-2,4-diones, herbicidal and plant growth-regulating agents containing these novel active ingredients, and processes for combating unwanted plant growth and for regulating plant growth.

It is known that tetrahydro(thio)pyran-2,4-dione oxime ether derivatives have a herbicidal action on monocotyledonous plants. Examples are tetrahydropyran-2,4-diones bearing aliphatic or aromatic substituents in the 6-position (GB-A-2 140 803; EP-A-0 164 056).

We have now found novel tetrahydro(thio)pyran-2,4-dione derivatives which have a good herbicidal action, particularly on grass species.

The formula of these tetrahydro(thio)pyran-2,4-diones is

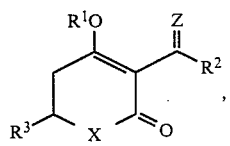

(I)

where $R^1$ is hydrogen, a cation, $C_1$–$C_{10}$-alkylcarbonyl, $C_2$–$C_{10}$-alkenylcarbonyl, or benzoyl which is unsubstituted or substituted in the phenyl ring by $C_1$–$C_8$-alkyl, $R^2$ is $C_1$–$C_5$-alkyl, $R^3$ is a non-aromatic, unsubstituted or $C_1$–$C_3$-alkyl-substituted heterocyclic compound of 5 to 7 ring members and having at most one double bond in the heterocyclic ring which contains up to two heteroatoms selected from the group consisting of sulfur and oxygen, X is oxygen or sulfur, and Z is oxygen or the radical NO—$R^4$, $R^4$ denoting $C_1$–$C_4$-alkyl, $C_3$–$C_4$-alkenyl, $C_3$–$C_4$-alkynyl, $C_2$–$C_4$-haloalkyl, $C_2$–$C_4$-haloalkenyl, $C_2$–$C_3$-alkoxyalkyl or the radical $CH_2$—$R^5$, where $R^5$ is a heterocyclic compound of 5 ring members and containing from 1 to 3 hetero-atoms, the number of nitrogen atoms being at most three, the number of oxygen atoms being at most two and the number of sulfur atoms being at most one, said heterocyclic compound containing from 0 to 2 double bonds and bearing either no substituents or one or two substituents selected from the group consisting of $C_1$–$C_4$-alkyl, $C_1$–$C_4$-alkoxy, halogen, trifluoromethyl, $C_1$–$C_4$-alkoxymethyl, $C_1$–$C_4$-alkylthiomethyl and vinyl, or $R^5$ is phenyl which is unsubstituted or bears from one to three substituents selected from the group consisting of $C_1$–$C_4$-alkyl, $C_1$–$C_4$-alkoxy, halogen, trifluoromethyl, nitro and $C_1$–$C_4$-dialkylamino.

The tetrahydro(thio)pyran-2,4-dione derivatives of the formula I in which Z is NO—$R^4$ have a good herbicidal action, whereas the tetrahydro(thio)pyran-2,4-dione derivatives of the formula I in which Z is oxygen preferentially exhibit growth-regulating properties.

The compounds of the formula I may occur in several tautomeric forms, all of which are encompassed by the claims. For example, the compounds in which $R^1$ is H and Z is NO—$R^4$ may occur in the following tautomeric forms:

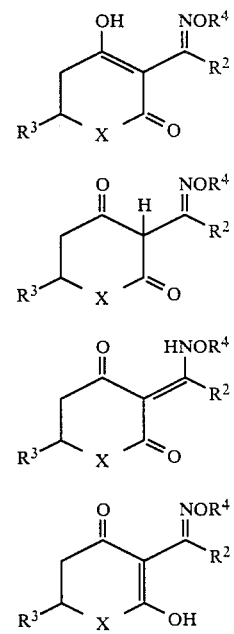

Where $R^4$ is $C_2$–$C_4$-haloalkyl or -alkenyl, these radicals contain from 1 to 4 halogen atoms. Where $R^4$ is $C_3$–$C_4$-alkenyl or $C_2$–$C_4$-haloalkenyl, the claims encompass both isomers in those cases in which E- and Z-isomers may occur.

In formula I, $R^1$ may denote hydrogen, $C_1$–$C_{10}$-alkylcarbonyl, preferably $C_1$–$C_4$-alkylcarbonyl, $C_2$–$C_{10}$-alkenylcarbonyl, preferably $C_2$–$C_4$-alkenylcarbonyl such as acetyl, propionyl, acroyl, butyryl, isobutyryl, pivaloyl, valeroyl, 2-ethylhexanoyl, caproyl, caprynoyl, lauryl, palmitoyl, stearoyl and oleoyl, $R^1$ may further denote benzoyl which is unsubstituted or substituted by $C_1$–$C_8$-alkyl, preferably $C_1$–$C_4$-alkyl, such as 4-methylbenzoyl, 4-hexylbenzoyl and benzoyl. Alkenylcarbonyl radicals which have only one C—C double bond are preferred.

In formula I, $R^2$ denotes for example methyl, ethyl, n-propyl, isopropyl, n-butyl, sec-butyl, isobutyl, tert-butyl or pentyl.

In formula I, $R^3$ denotes a non-aromatic heterocyclic compound having 5 to 7 members and at most one double bond. The number of hetero-atoms is restricted to a maximum of two selected from the group consisting of oxygen and sulfur. These heterocyclic radicals may be substituted by $C_1$–$C_3$-alkyl. Examples of meanings for $R^3$ are $C_1$–$C_3$-alkyl-substituted tetrahydropyranyl, tetrahydrothiopyranyl, 5,6-dihydro-2H-pyranyl, 5,6-dihydro-2H-thiopyranyl, tetrahydrofuranyl or 1,3-dioxepanyl, such as tetrahydropyran-3-yl, tetrahydropyran-4-yl, tetrahydrothiopyran-3-yl, tetrahydrothiopyran-4-yl, 5,6-dihydro-2H-pyran-3-yl, 5,6-dihydro-2H-thiopyran-3-yl, 1,4-dioxanyl, 5,6-dihydro-2H-2,6-dimethylpyran-3-yl, tetrahydrofuran-2-yl, tetrahydrofuran-3-yl, 2-isopropyl-1,3-dioxepan-5-yl, and 2-methyl-1,3-dioxepan-5-yl.

When Z is NO—$R^4$, $R^4$ denotes, for example $C_1$–$C_4$-alkyl, $C_3$–$C_4$-alkenyl, $C_3$–$C_4$-alkynyl, $C_2$–$C_4$-haloalkyl or $C_2$–$C_4$-haloalkenyl, each having preferably from 1 to 3 halogen atoms selected from the group consisting of fluorine and chlorine, or $C_2$–$C_3$-alkoxyalkyl, for example methyl, ethyl, propyl, allyl, (E)-but-2-en-1-yl, propargyl, 2-chloroallyl, (E)-3-chloroprop-1-enyl, 3-fluoropropyl and 2-methoxyethyl, or $R^4$ is the radical $CH_2-R^5$, $R^5$ denoting a 5-membered heterocyclic compound having 1 to 3 hetero-atoms and 0, 1 or 2 double bonds. These hetero-atoms may be nitrogen, sulfur or oxygen atoms, the number of nitrogen atoms being at most three, the number of oxygen atoms being at most two and the number of sulfur atoms being at most one. These heterocyclic radicals are unsubstituted or bear up to two substituents selected from the group consisting of $C_1-C_4$-alkyl, $C_1-C_4$-alkoxy, halogen, trifluoromethyl, $C_1-C_4$-alkoxymethyl, $C_1-C_4$-alkylthiomethyl and vinyl. $R^5$ may also be phenyl which is unsubstituted or bears up to three substituents selected from the group consisting of $C_1-C_4$-alkyl, $C_1-C_4$-alkoxy, halogen, trifluoromethyl, nitro and $C_1-C_4$-dialkylamino. Examples of $R^5$ are p-fluorophenyl, phenyl, thien-2-yl, m-trifluoromethylphenyl, p-nitrophenyl, and 5-chlorothien-2-yl.

Examples of suitable salts of compounds of the formula I ($R^1$=cation) are agriculturally useful salts such as alkali metal salts, especially potassium and sodium salts, alkaline earth metal salts, especially calcium, manganese, copper, zinc and iron salts, ammonium, sulfonium, sulfoxonium and phosphonium salts, for example ammonium, tetraalkylammonium, benzyltrialkylammonium, trialkylsulfoxonium and trialkylsulfonium salts.

Preferred tetrahydro(thio)pyran-2,4-dione derivatives of the formula I are those in which $R^2$ is $C_2-C_3$-alkyl. Compounds of the formula I in which X is oxygen are also preferred.

Tetrahydro(thio)pyran-2,4-dione derivatives of the formula I in which Z is $NOR^4$ may be obtained by reaction of tetrahydro(thio)pyan-2,4-dione derivatives of the formula I in which Z is oxygen with an ammonium compound of the formula $[R^4O-NH_3]Y$, where $R^4$ has the above meanings and Y is an anion (chloride, bromide or sulfate).

The reaction is advantageously carried out in the heterogeneous phase in an inert solvent and at a temperature of from 0° to 80° C., or from 0° C. to the boiling point of the reaction mixture in the presence of a base. Examples of suitable bases are carbonates, bicarbonates, acetates, alcoholates, hydroxides and oxides of alkali metals or alkaline earth metals, especially sodium hydroxide, potassium hydroxide, magnesium oxide and calcium oxide. Organic bases such as pyridine and tertiary amines may also be used. The base is employed in amounts of from 0.5 to 2 moles, based on the ammonium compound (DE-A-3 433 767).

Examples of suitable solvents are dimethyl sulfoxide; alcohols such as methanol, ethanol and isopropanol; toluene; hydrocarbons and chlorohydrocarbons such as chloroform, dichloromethane, hexane and cyclohexane; esters such as ethyl acetate; and ethers such as dioxane and tetrahydrofuran.

Tetrahydro(thio)pyran-2,4-dione derivatives of the formula I in which Z is oxygen are obtained in conventional manner by reacting tetrahydro(thio)pyran-2,4-dione derviatives of the formula

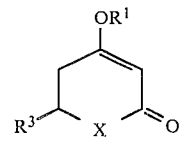

where $R^1$ is hydrogen and $R^3$ and X have the above meanings, with acid chlorides of the formula $R^2-COCl$, where $R^2$ has the above meanings, in the presence of a base (e.g., triethylamine) and an inert diluent (e.g., tetrahydrofuran) to give the enol ester, and treating it with an acidic or basic catalyst in an inert solvent (e.g., ethyl acetate, toluene) at from 0° to 100° C. (JP-A-63052/79). Examples of acidic or basic catalysts are aluminum chloride, iron chloride, imidazole derivatives, e.g., imidazole, and pyridine derivatives, e.g., dimethylaminopyridine.

For the manufacture of the compounds of the formula II several processes are known from the literature:

(a) Reaction of a 4-bromo-3-methoxycrotonate of the formula III, R denoting methyl, ethyl or propyl, with an aldehyde of the formula $R^3-CHO$, $R^3$ having the above meanings, in an inert solvent (e.g., chlorine, tetrahydrofuran, benzene) in the presence of zinc (J. Heterocyclic Chem., 21, 1755, 1984).

(b) Reaction of diketene with an aldehyde of the formula $R^3-CHO$, $R^3$ having the above meanings, in an inert solvent (e.g., dichloromethane) with a Lewis acid (e.g., titanium tetrachloride) as catalyst (Chem. Letters, 1975, 101).

(c) Reaction of the dianion of an ethyl acetoacetate of the formula IV, R denoting methyl, ethyl or propyl, with an aldehyde of the formula $R^3-CHO$, $R^3$ having the above meanings, in an inert solvent, e.g., tetrahydrofuran (Angew. Chem., 86, 40, 1974).

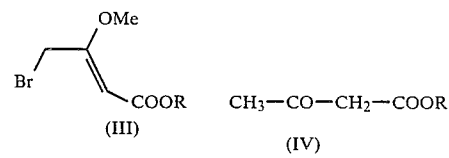

Compounds of the formula IIa below in which $R^1$ is hydrogen and X is sulfur and $R^3$ has the above meanings are obtained by reacting vinyl ketones of the formula V, $R^3$ having the above meanings, with dialkylammonium dithiocarbamates of the formula VI in an inert solvent (e.g., dimethylformamide, chlorobenzene, xylene, toluene) at from 80° to 100° C. The dihydrothiopyran derivative of the formula VII which is formed is converted by treatment with an aqueous solution (e.g., sodium hydroxide, potassium hydroxide) and alkaline hydrogen peroxide into the tetrahydrothiopyran-2,4-dione derivatives of the formula IIa in which $R^1$ is hydrogen and $R^3$ has the above meanings (Monatshefte f. Chem., 113, 1983, 1982, and 111, 1175, 1980).

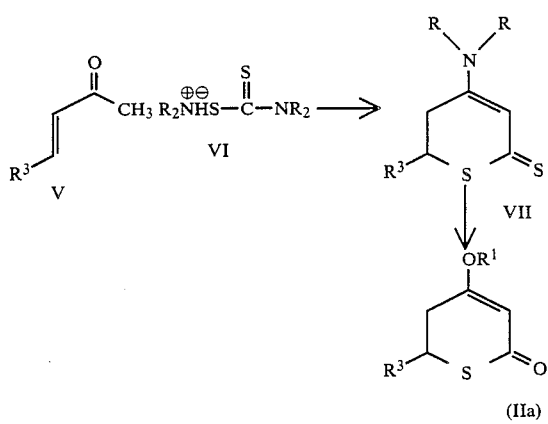

The α,β-unsaturated compounds of the formulae III and V may be present as cis and trans isomers.

Aldehydes of the formula $R^3$—CHO are obtained by conventional methods, e.g., by oxidation of alcohols, reduction of carboxylic acid derivatives or hydroformylation of olefins.

MANUFACTURING EXAMPLE

(a) Methyl 5-hydroxy-3-oxo-5-(tetrahydrothiopyran-3-yl)-pentanoate 6.6 g of sodium hydride (80%) is added to 400 ml of tetrahydrofuran and the mixture is cooled to 0° C. At this temperature, 24.4 g of methyl acetoacetate is dripped in, the resulting mixture is stirred for 15 minutes, then 137.5 ml of a 1.6 molar butyllithium solution in hexane is dripped in and the mixture stirred for 30 minutes. At from 0° to 3° C., 26 g of tetrahydrothiopyran-3-carboaldehyde is dripped in and the mixture stirred for a further 30 minutes to complete the reaction. To this end, 45 ml of concentrated hydrochloric acid is carefully dripped in. The cold reaction mixture is poured into 250 ml of ice water and the organic phase is separated. The aqueous phase is extracted twice, each time with 250 ml of methyl tert-butyl ether. The combined organic extracts are washed once with 300 ml of saturated sodium chloride solution, dried with sodium sulfate and concentrated in a rotary evaporator. There is obtained 48.1 g of an oil which is used immediately for further reaction.

(b) 5-(Tetrahydrothiopyran-3-yl)-tetrahydropyran-2,4-dione 48 g of methyl 5-hydroxy-3-oxo-5-(tetrahydrothiopyran-3-yl)-pentanoate is stirred for 16 hours in 300 ml of 5% strength sodium hydroxide solution. The aqueous solution is purified by extracting twice with 250 ml of toluene. While cooling with ice, the aqueous phase is acidified to pH 1 with concentrated hydrochloric acid. The precipitate is suction filtered and stirred with ether. The residue is suction filtered and dried. There is obtained 27 g of a solid which melts at 91° to 93° C.

(c) 3-Propionyl-5-(tetrahydrothiopyran-3-yl)-tetrahydropyran-2,4-dione 2.4 g of triethylamine is added to 5 g of 5-(tetrahydrothiopyran-3-yl)-tetrahydropyran-2,4-dione in 50 ml of anhydrous tetrahydrofuran. At 0° C., 2.2 g of propionyl chloride is dripped in and the mixture is stirred for 12 hours at room temperature. The mixture is then diluted with 150 ml of water, and the aqueous phase is separated and extracted with 100 ml of ether. The combined organic phases are washed once with ice-cold 5% strength hydrochloric acid and once with water, and dried with magnesium sulfate, and the solvent is removed. The oily residue is dissolved in 50 ml of anhydrous toluene, 0.3 g of 3-dimethylaminopyridine is added, and the mixture is stirred at 80° C. for 2 hours. After cooling, extraction is carried out twice with 25 ml of hydrochloric acid and twice with 25 ml of water. The organic phase is dried over sodium sulfate and concentrated in a rotary evaportor. The residue is chromatographed with methylene chloride on silica gel. There is obtained 1.8 g of the desired compound.

(d) 3-(1-Ethoxyiminopropyl)-5-(tetrahydrothiopyran-3-yl)-tetrahydropyran-2,4-dione (compound no. 36 in Table 1)

0.6 g of sodium bicarbonate and subsequently 0.7 g of ethoxyamine hydrochloride are added to a solution of 1.6 g of 3-propionyl-5-(tetrahydrothiopyran-3-yl)-tetrahydropyran-2,4-dione in 25 ml of anhydrous methanol. The reaction mixture is stirred for 12 hours at room temperature and then evaporated to dryness. The residue is taken up in 50 ml of methylene chloride, and washed once with water, twice with saturated sodium bicarbonate solution and again with water. The organic phase is dried with sodium sulfate and the solvent is stripped off. There is obtained 0.8 g of oxime ether.

The compounds of the formula I given in the following tables may be obtained analogously.

TABLE 1

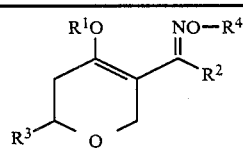

| No. | $R^3$ | $R^2$ | $R^1$ | $R^4$ | Physical data |
|---|---|---|---|---|---|
| 1 | tetrahydropyran-3-yl | ethyl | H | ethyl | |
| 2 | tetrahydropyran-3-yl | ethyl | H | allyl | |
| 3 | tetrahydropyran-3-yl | ethyl | H | (E)-3-chloroallyl | 3-chloroallyl |
| 4 | tetrahydropyran-3-yl | ethyl | H | (E)-2-butenyl | |
| 5 | tetrahydropyran-3-yl | ethyl | H | thien-2-ylmethyl | |

TABLE 1-continued

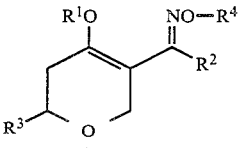

(Ia)

| No. | R³ | R² | R¹ | R⁴ | Physical data |
|---|---|---|---|---|---|
| 6 | tetrahydropyran-3-yl | ethyl | H | 5-chlorothien-2-ylmethyl | |
| 7 | tetrahydropyran-3-yl | ethyl | H | p-fluoromethylphenylmethyl | |
| 8 | tetrahydropyran-3-yl | ethyl | H | m-trifluoromethylphenylmethyl | |
| 9 | tetrahydropyran-3-yl | ethyl | H | p-nitrophenylmethyl | |
| 10 | tetrahydropyran-3-yl | ethyl | acetyl | allyl | |
| 11 | tetrahydropyran-3-yl | ethyl | acetyl | (E)-3-chloroallyl | |
| 12 | tetrahydropyran-3-yl | ethyl | acetyl | p-fluorophenylmethyl | |
| 13 | tetrahydropyran-3-yl | ethyl | benzoyl | allyl | |
| 14 | tetrahydropyran-3-yl | ethyl | benzoyl | (E)-3-chloroallyl | |
| 15 | tetrahydropyran-3-yl | ethyl | benzoyl | m-trifluoromethylphenylmethyl | |
| 16 | tetrahydropyran-3-yl | propyl | H | ethyl | NMR: 4.1–4.3, m; 4.05–4.2, q; 3.8–4.0, m; 1.25–1.4, t; 0.8–1.1, t; |
| 17 | tetrahydropyran-3-yl | propyl | H | allyl | |
| 18 | tetrahydropyran-3-yl | propyl | H | (E)-3-chloroallyl | |
| 19 | tetrahydropyran-3-yl | propyl | H | (E)-2-butenyl | |
| 20 | tetrahydropyran-3-yl | propyl | H | thien-2-ylmethyl | |
| 21 | tetrahydropyran-3-yl | propyl | H | 5-chlorothien-2-ylmethyl | |
| 22 | tetrahydropyran-3-yl | propyl | H | p-fluorophenylmethyl | |
| 23 | tetrahydropyran-3-yl | propyl | H | m-trifluoromethylphenylmethyl | |
| 24 | tetrahydropyran-3-yl | propyl | H | p-nitrophenylmethyl | |
| 25 | tetrahydropyran-3-yl | propyl | acetyl | ethyl | |
| 26 | tetrahydropyran-3-yl | propyl | acetyl | allyl | |
| 27 | tetrahydropyran-3-yl | propyl | acetyl | methoxymethyl | |
| 28 | tetrahydropyran-3-yl | propyl | benzoyl | ethyl | |
| 29 | tetrahydropyran-3-yl | propyl | benzoyl | allyl | |
| 30 | tetrahydropyran-3-yl | propyl | benzoyl | 2-methoxyethyl | |
| 31 | tetrahydropyran-3-yl | pentyl | H | ethyl | |
| 32 | tetrahydropyran-3-yl | pentyl | H | allyl | |
| 33 | tetrahydropyran-3-yl | pentyl | H | (E)-3-chloroallyl | |
| 34 | tetrahydropyran-3-yl | pentyl | acetyl | ethyl | |
| 35 | tetrahydropyran-3-yl | pentyl | benzoyl | ethyl | |
| 36 | tetrahydrothiopyran-3-yl | ethyl | H | ethyl | NMR: 1.19, t; 1.36, t; 4.13, q; 4.2–4.3, m; |
| 37 | tetrahydrothiopyran-3-yl | ethyl | H | allyl | NMR: 1.19, t; 4.15–4.3, m; 4.56, d; 5.3–5.5, m; 5.9–6.1, m |
| 38 | tetrahydrothiopyran-3-yl | ethyl | H | (E)-3-chloroallyl | NMR: 6.0–6.4, m; 4.45–4.55, d; 4.15–4.3, m; 1.1–1.2, d |
| 39 | tetrahydrothiopyran-3-yl | ethyl | H | (E)-2-butenyl | |
| 40 | tetrahydrothiopyran-3-yl | ethyl | H | thien-2-ylmethyl | |
| 41 | tetrahydrothiopyran-3-yl | ethyl | H | 5-chlorothien-2-ylmethyl | |
| 42 | tetrahydrothiopyran-3-yl | ethyl | H | p-fluorophenylmethyl | |
| 43 | tetrahydrothiopyran-3-yl | ethyl | H | m-trifluoromethylphenylmethyl | |
| 44 | tetrahydrothiopyran-3-yl | ethyl | H | p-nitrophenylmethyl | |
| 45 | tetrahydrothiopyran-3-yl | ethyl | acetyl | allyl | |
| 46 | tetrahydrothiopyran-3-yl | ethyl | acetyl | (E)-3-chloroallyl | |
| 47 | tetrahydrothiopyran-3-yl | ethyl | acetyl | p-fluorophenylmethyl | |
| 48 | tetrahydrothiopyran-3-yl | ethyl | benzoyl | allyl | |
| 49 | tetrahydrothiopyran-3-yl | ethyl | benzoyl | (E)-3-chloroallyl | |
| 50 | tetrahydrothiopyran-3-yl | ethyl | benzoyl | m-trifluoromethylphenylmethyl | |
| 51 | tetrahydrothiopyran-3-yl | propyl | H | ethyl | NMR: 4.1–4.3, m; 4.0–4.2, q; 2.95–3.1, m; 1.3–1.4, t; 0.9–1.1, t |
| 52 | tetrahydrothiopyran-3-yl | propyl | H | allyl | NMR: 0.98, t; 4.1–4.3, m 4.55, d; 5.2–5.5, m; 5.9–6.1, m; |
| 53 | tetrahydrothiopyran-3-yl | propyl | H | (E)-3-chloroallyl | NMR: 0.98, t; 4.1–4.3, m; 4.53, d; 6.0–6.2, m; 6.3–6.45, 2, m; |
| 54 | tetrahydrothiopyran-3-yl | propyl | H | (E)-2-butenyl | NMR: 1.0, t; 1.8, |

TABLE 1-continued (Ia)

$$\begin{array}{c} R^1O \quad NO-R^4 \\ \diagdown \quad \| \\ R^2 \\ R^3 \quad O \end{array}$$

| No. | R³ | R² | R¹ | R⁴ | Physical data |
|---|---|---|---|---|---|
| | | | | | d; 4.1–4.3, m; 4.45, 5.5–5.7, m; 5.8–6.0, m, |
| 55 | tetrahydrothiopyran-3-yl | propyl | H | thien-2-ylmethyl | NMR; 0.95, t; 4.1–4.3, m; 5.2, s; 7.04, dd; 7.12, d; 7.37, d; |
| 56 | tetrahydrothiopyran-3-yl | propyl | H | 5-chlorothien-2-ylmethyl | NMR; 0.99, t; 4.15–4.3, m; 5.1, s; 6.8–6.9, m; |
| 57 | tetrahydrothiopyran-3-yl | propyl | H | p-fluorphenylmethyl | |
| 58 | tetrahydrothiopyran-3-yl | propyl | H | m-trifluormethylphenylmethyl | NMR; 0.97, t; 4.1–4.25, m; 5.12, dd; 7.4–7.7, m; |
| 59 | tetrahydrothiopyran-3-yl | propyl | H | p-nitrophenylmethyl | |
| 60 | tetrahydrothiopyran-3-yl | propyl | acetyl | ethyl | |
| 61 | tetrahydrothiopyran-3-yl | propyl | acetyl | allyl | |
| 62 | tetrahydrothiopyran-3-yl | propyl | acetyl | 3-fluoropropyl | |
| 63 | tetrahydrothiopyran-3-yl | propyl | benzoyl | ethyl | |
| 64 | tetrahydrothiopyran-3-yl | propyl | benzoyl | allyl | |
| 65 | tetrahydrothiopyran-3-yl | propyl | benzoyl | phenylmethyl | |
| 66 | tetrahydrothiopyran-3-yl | pentyl | H | ethyl | |
| 67 | tetrahydrothiopyran-3-yl | pentyl | H | allyl | |
| 68 | tetrahydrothiopyran-3-yl | pentyl | H | (E)-3-chloroallyl | |
| 69 | tetrahydrothiopyran-3-yl | pentyl | acetyl | ethyl | |
| 70 | tetrahydrothiopyran-3-yl | pentyl | benzoyl | ethyl | |
| 71 | tetrahydropyran-4-yl | ethyl | H | ethyl | NMR; 1.21, t; 1.33, t; 3.4, dd; 3.95–4.25, m; |
| 72 | tetrahydropyran-4-yl | ethyl | H | allyl | |
| 73 | tetrahydropyran-4-yl | ethyl | H | (E)-3-chloroallyl | |
| 74 | tetrahydropyran-4-yl | ethyl | H | (E)-2-butenyl | |
| 75 | tetrahydropyran-4-yl | ethyl | H | 5-chlorothien-2-yl | |
| 76 | tetrahydropyran-4-yl | ethyl | H | m-trifluoromethylphenylmethyl | NMR; 1.19, t; 2.8–3.1, m; 3.3–3.5, m; 3.9–4.2, m; 5.15, s; 7.4–7.75, m; |
| 77 | tetrahydropyran-4-yl | ethyl | acetyl | allyl | |
| 78 | tetrahydropyran-4-yl | ethyl | benzoyl | allyl | |
| 79 | tetrahydropyran-4-yl | propyl | H | ethyl | |
| 80 | tetrahydropyran-4-yl | propyl | H | allyl | |
| 81 | tetrahydropyran-4-yl | propyl | H | (E)-3-chloroallyl | |
| 82 | tetrahydropyran-4-yl | propyl | H | 5-chlorothien-2-ylmethyl | |
| 83 | tetrahydropyran-4-yl | propyl | H | p-fluorophenylmethyl | |
| 84 | tetrahydropyran-4-yl | propyl | acetyl | ethyl | |
| 85 | tetrahydropyran-4-yl | propyl | benzoyl | ethyl | |
| 86 | tetrahydrothiopyran-4-yl | ethyl | H | allyl | |
| 87 | tetrahydrothiopyran-4-yl | ethyl | H | (E)-3-chloroallyl | |
| 88 | tetrahydrothiopyran-4-yl | ethyl | H | 3-fluoropropyl | |
| 89 | tetrahydrothiopyran-4-yl | ethyl | H | 5-chlorothien-2-ylmethyl | |
| 90 | tetrahydrothiopyran-4-yl | ethyl | H | p-nitrophenylmethyl | |
| 91 | tetrahydrothiopyran-4-yl | ethyl | acetyl | allyl | |
| 92 | tetrahydrothiopyran-4-yl | ethyl | benzoyl | allyl | |
| 93 | tetrahydrothiopyran-4-yl | propyl | H | ethyl | |
| 94 | tetrahydrothiopyran-4-yl | propyl | H | allyl | |
| 95 | tetrahydrothiopyran-4-yl | propyl | H | (E)-3-chloroallyl | |
| 96 | tetrahydrothiopyran-4-yl | propyl | H | p-fluorophenylmethyl | |
| 97 | tetrahydrothiopyran-4-yl | propyl | H | p-nitrophenylmethyl | |
| 98 | tetrahydrothiopyran-4-yl | propyl | acetyl | ethyl | |
| 99 | tetrahydrothiopyran-4-yl | propyl | benzoyl | ethyl | |
| 100 | 5,6-dihydro-2H-pyran-3-yl | ethyl | H | allyl | |
| 101 | 5,6-dihydro-2H-pyran-3-yl | ethyl | H | (E)-3-chloroallyl | |
| 102 | 5,6-dihydro-2H-pyran-3-yl | ethyl | H | (E)-2-butenyl | |
| 103 | 5,6-dihydro-2H-pyran-3-yl | ethyl | H | phenylmethyl | |
| 104 | 5,6-dihydro-2H-pyran-3-yl | ethyl | acetyl | allyl | |
| 105 | 5,6-dihydro-2H-pyran-3-yl | ethyl | benzoyl | allyl | |
| 106 | 5,6-dihydro-2H-pyran-3-yl | propyl | H | ethyl | |
| 107 | 5,6-dihydro-2H-pyran-3-yl | propyl | H | allyl | |
| 108 | 5,6-dihydro-2H-pyran-3-yl | propyl | H | (E)-3-chloroallyl | |
| 109 | 5,6-dihydro-2H-pyran-3-yl | propyl | H | 2-chloroallyl | |

TABLE 1-continued $$\text{(Ia)}$$

| No. | R³ | R² | R¹ | R⁴ | Physical data |
|---|---|---|---|---|---|
| 110 | 5,6-dihydro-2H-pyran-3-yl | propyl | acetyl | ethyl | |
| 111 | 5,6-dihydro-2H-pyran-3-yl | propyl | benzoyl | ethyl | |
| 112 | 5,6-dihydro-2H-thiopyran-3-yl | ethyl | H | allyl | |
| 113 | 5,6-dihydro-2H-thiopyran-3-yl | ethyl | H | (E)-3-chloroallyl | |
| 114 | 5,6-dihydro-2H-thiopyran-3-yl | ethyl | H | (E)-2-butenyl | |
| 115 | 5,6-dihydro-2H-thiopyran-3-yl | ethyl | H | 5-chlorothien-2-ylmethyl | |
| 116 | 5,6-dihydro-2H-thiopyran-3-yl | ethyl | acetyl | (E)-3-chloroallyl | |
| 117 | 5,6-dihydro-2H-thiopyran-3-yl | ethyl | benzoyl | (E)-3-chloroallyl | |
| 118 | 5,6-dihydro-2H-thiopyran-3-yl | propyl | H | ethyl | |
| 119 | 5,6-dihydro-2H-thiopyran-3-yl | propyl | H | allyl | |
| 120 | 5,6-dihydro-2H-thiopyran-3-yl | propyl | H | (E)-3-chloroallyl | |
| 121 | 5,6-dihydro-2H-thiopyran-3-yl | propyl | H | 5-chlorothien-2-ylmethyl | |
| 122 | 5,6-dihydro-2H-thiopyran-3-yl | propyl | acetyl | ethyl | |
| 123 | 5,6-dihydro-2H-thiopyran-3-yl | propyl | benzoyl | ethyl | |
| 124 | 5,6-dihydro-2,6-dimethyl-2H-pyran-3-yl | ethyl | H | ethyl | |
| 125 | 5,6-dihydro-2,6-dimethyl-2H-pyran-3-yl | ethyl | H | allyl | |
| 126 | 5,6-dihydro-2,6-dimethyl-2H-pyran-3-yl | ethyl | H | (E)-3-chloroallyl | |
| 127 | 5,6-dihydro-2,6-dimethyl-2H-pyran-3-yl | ethyl | H | (E)-2-butenyl | |
| 128 | 5,6-dihydro-2,6-dimethyl-2H-pyran-3-yl | ethyl | H | p-fluorophenylmethyl | |
| 129 | 5,6-dihydro-2,6-dimethyl-2H-pyran-3-yl | ethyl | H | p-nitrophenylmethyl | |
| 130 | 5,6-dihydro-2,6-dimethyl-2H-pyran-3-yl | ethyl | acetyl | (E)-3-chloroallyl | |
| 131 | 5,6-dihydro-2,6-dimethyl-2H-pyran-3-yl | ethyl | benzoyl | (E)-3-chloroallyl | |
| 132 | 5,6-dihydro-2,6-dimethyl-2H-pyran-3-yl | propyl | H | ethyl | |
| 133 | 5,6-dihydro-2,6-dimethyl-2H-pyran-3-yl | propyl | H | allyl | |
| 134 | 5,6-dihydro-2,6-dimethyl-2H-pyran-3-yl | propyl | H | (E)-3-chloroallyl | |
| 135 | 5,6-dihydro-2,6-dimethyl-2H-pyran-3-yl | propyl | H | (E)-2-butenyl | |
| 136 | 5,6-dihydro-2,6-dimethyl-2H-pyran-3-yl | propyl | H | p-fluorophenylmethyl | |
| 137 | 5,6-dihydro-2,6-dimethyl-2H-pyran-3-yl | propyl | H | p-nitropehnylmethyl | |
| 138 | 5,6-dihydro-2,6-dimethyl-2H-pyran-3-yl | propyl | acetyl | ethyl | |
| 139 | 5,6-dihydro-2,6-dimethyl-2H-pyran-3-yl | propyl | benzoyl | ethyl | |
| 140 | 1,4-dioxanyl | ethyl | H | allyl | |
| 141 | 1,4-dioxanyl | ethyl | H | (E)-3-chloroallyl | |
| 142 | 1,4-dioxanyl | ethyl | H | (E)-2-butenyl | |
| 143 | 1,4-dioxanyl | ethyl | H | 5-chlorothien-2-ylmethyl | |
| 144 | 1,4-dioxanyl | propyl | H | ethyl | |
| 145 | 1,4-dioxanyl | propyl | H | allyl | |
| 146 | 1,4-dioxanyl | propyl | H | (E)-3-chloroallyl | |
| 147 | 1,4-dioxanyl | propyl | H | 5-chlorothien-2-ylmethyl | |
| 148 | tetrahydrofuran-2-yl | ethyl | H | allyl | |
| 149 | tetrahydrofuran-2-yl | ethyl | H | (E)-3-chloroallyl | |
| 150 | tetrahydrofuran-2-yl | ethyl | H | (E)-2-butenyl | |
| 151 | tetrahydrofuran-2-yl | ethyl | H | p-nitrophenylmethyl | |
| 152 | tetrahydrofuran-2-yl | propyl | H | ethyl | |
| 153 | tetrahydrofuran-2-yl | propyl | H | allyl | |
| 154 | tetrahydrofuran-2-yl | propyl | H | (E)-3-chloroallyl | |
| 155 | tetrahydrofuran-2-yl | propyl | H | p-nitrophenylmethyl | |
| 156 | tetrahydrofuran-2-yl | ethyl | H | allyl | |
| 157 | tetrahydrofuran-2-yl | ethyl | H | (E)-3-chloroallyl | |
| 158 | tetrahydrofuran-2-yl | ethyl | H | (E)-2-butenyl | |
| 159 | tetrahydrofuran-2-yl | ethyl | H | p-fluorophenylmethyl | |
| 160 | tetrahydrofuran-2-yl | propyl | H | ethyl | |
| 161 | tetrahydrofuran-2-yl | propyl | H | allyl | |
| 162 | tetrahydrofuran-2-yl | propyl | H | (E)-3-chloroallyl | |
| 163 | tetrahydrofuran-2-yl | propyl | H | p-fluorophenylmethyl | |
| 164 | 2-isopropyl-1,3-dioxepan-5-yl | ethyl | H | ethyl | |
| 165 | 2-isopropyl-1,3-dioxepan-5-yl | ethyl | H | allyl | |
| 166 | 2-isopropyl-1,3-dioxepan-5-yl | ethyl | H | (E)-3-chloroallyl | |
| 167 | 2-isopropyl-1,3-dioxepan-5-yl | ethyl | H | (E)-2-butenyl | |
| 168 | 2-isopropyl-1,3-dioxepan-5-yl | ethyl | H | p-fluorophenylmethyl | |
| 169 | 2-isopropyl-1,3-dioxepan-5-yl | ethyl | H | p-nitrophenylmethyl | |
| 170 | 2-isopropyl-1,3-dioxepan-5-yl | ethyl | H | 5-chlorothien-2-ylmethyl | |
| 171 | 2-isopropyl-1,3-dioxepan-5-yl | ethyl | H | m-trifluoromethylphenylmethyl | |
| 172 | 2-isopropyl-1,3-dioxepan-5-yl | propyl | H | ethyl | |
| 173 | 2-isopropyl-1,3-dioxepan-5-yl | propyl | H | allyl | |
| 174 | 2-isopropyl-1,3-dioxepan-5-yl | propyl | H | (E)-3-chloroallyl | |
| 175 | 2-isopropyl-1,3-dioxepan-5-yl | propyl | H | (E)-2-butenyl | |
| 176 | 2-isopropyl-1,3-dioxepan-5-yl | propyl | H | p-fluorophenylmethyl | |
| 177 | 2-isopropyl-1,3-dioxepan-5-yl | propyl | H | p-nitrophenylmethyl | |
| 178 | 2-isopropyl-1,3-dioxepan-5-yl | propyl | H | 5-chlorothien-2-ylmethyl | |
| 179 | 2-isopropyl-1,3-dioxepan-5-yl | propyl | H | m-trifluoromethylphenylmethyl | |
| 180 | 2-methyl-1,3-dioxepan-5-yl | ethyl | H | ethyl | |
| 181 | 2-methyl-1,3-dioxepan-5-yl | ethyl | H | allyl | |

TABLE 1-continued

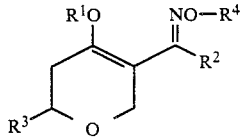
(Ia)

| No. | R³ | R² | R¹ | R⁴ | Physical data |
|---|---|---|---|---|---|
| 182 | 2-methyl-1,3-dioxepan-5-yl | ethyl | H | (E)-3-chloroallyl | |
| 183 | 2-methyl-1,3-dioxepan-5-yl | ethyl | H | (E)-2-butenyl | |
| 184 | 2-methyl-1,3-dioxepan-5-yl | ethyl | H | p-fluorophenylmethyl | |
| 185 | 2-methyl-1,3-dioxepan-5-yl | ethyl | H | p-nitrophenylmethyl | |
| 186 | 2-methyl-1,3-dioxepan-5-yl | propyl | H | ethyl | |
| 187 | 2-methyl-1,3-dioxepan-5-yl | propyl | H | allyl | |
| 188 | 2-methyl-1,3-dioxepan-5-yl | propyl | H | (E)-3-chloroallyl | |
| 189 | 2-methyl-1,3-dioxepan-5-yl | propyl | H | (E)-2-butenyl | |
| 190 | 2-methyl-1,3-dioxepan-5-yl | propyl | H | p-fluorophenylmethyl | |
| 191 | 2-methyl-1,3-dioxepan-5-yl | propyl | H | p-nitrophenylmethyl | |

TABLE 2

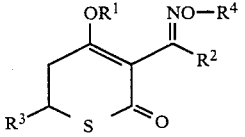
(Ib)

| No. | R³ | R² | R¹ | R⁴ | Phys. data |
|---|---|---|---|---|---|
| 192 | tetrahydropyran-3-yl | ethyl | H | ethyl | |
| 193 | tetrahydropyran-3-yl | ethyl | H | allyl | |
| 194 | tetrahydropyran-3-yl | ethyl | H | (E)—3-chloroallyl | |
| 195 | tetrahydropyran-3-yl | ethyl | H | (E)—2-butenyl | |
| 196 | tetrahydropyran-3-yl | ethyl | H | p-fluorophenylmethyl | |
| 197 | tetrahydropyran-3-yl | propyl | H | ethyl | |
| 198 | tetrahydropyran-3-yl | propyl | H | allyl | |
| 199 | tetrahydropyran-3-yl | propyl | H | (E)—3-chloroallyl | |
| 200 | tetrahydropyran-3-yl | propyl | H | p-flurorphenylmethyl | |
| 201 | tetrahydropyran-3-yl | propyl | H | m-trifluoromethylphenylmethyl | |
| 202 | tetrahydrothiopyran-3-yl | ethyl | H | ethyl | |
| 203 | tetrahydrothiopyran-3-yl | ethyl | H | allyl | |
| 204 | tetrahydrothiopyran-3-yl | ethyl | H | (E)—3-chloroallyl | |
| 205 | tetrahydrothiopyran-3-yl | ethyl | H | (E)—3-butenyl | |
| 206 | tetrahydrothiopyran-3-yl | ethyl | H | 5-chlorothien-2-ylmethyl | |
| 207 | tetrahydrothiopyran-3-yl | propyl | H | ethyl | |
| 208 | tetrahydrothiopyran-3-yl | propyl | H | allyl | |
| 209 | tetrahydrothiopyran-3-yl | propyl | H | (E)—3-chloroallyl | |
| 210 | tetrahydrothiopyran-3-yl | propyl | H | 5-chlorothien-2-ylmethyl | |
| 211 | tetrahydrothiopyran-3-yl | propyl | H | p-nitrophenylmethyl | |
| 212 | tetrahydro-pyran-4-yl | ethyl | H | ethyl | |
| 213 | tetrahydro-pyran-4-yl | ethyl | H | allyl | |
| 214 | tetrahydro-pyran-4-yl | ethyl | H | (E)—3-chloroallyl | |
| 215 | tetrahydro-pyran-4-yl | ethyl | H | (E)—2-butenyl | |
| 216 | tetrahydro-pyran-4-yl | ethyl | H | p-fluorophenylmethyl | |
| 217 | tetrahydro-pyran-4-yl | propyl | H | ethyl | |
| 218 | tetrahydro-pyran-4-yl | propyl | H | allyl | |
| 219 | tetrahydro-pyran-4-yl | propyl | H | (E)—3-chloroallyl | |
| 220 | tetrahydro-pyran-4-yl | propyl | H | (E)—3-butenyl | |
| 221 | tetrahydro-pyran-4-yl | propyl | H | p-fluorophenylmethyl | |
| 222 | 5,6-dihydro-2H—pyran-3-yl | ethyl | H | ethyl | |
| 223 | 5,6-dihydro-2H—pyran-3-yl | ethyl | H | allyl | |
| 224 | 5,6-dihydro-2H—pyran-3-yl | ethyl | H | (E)—3-chloroallyl | |
| 225 | 5,6-dihydro-2H—pyran-3-yl | ethyl | H | (E)—2-butenyl | |
| 226 | 5,6-dihydro-2H—pyran-3-yl | ethyl | H | m-trifluoromethylphenylmethyl | |
| 227 | 5,6-dihydro-2H—pyran-3-yl | ethyl | H | ethyl | |
| 228 | 5,6-dihydro-2H—pyran-3-yl | propyl | H | allyl | |
| 229 | 5,6-dihydro-2H—pyran-3-yl | propyl | H | (E)—3-chloroallyl | |
| 230 | 5,6-dihydro-2H—pyran-3-yl | propyl | H | (E)—2-butenyl | |
| 231 | 5,6-dihydro-2H—pyran-3-yl | propyl | H | m-trifluoromethylphenylmethyl | |
| 232 | 5,6-dihydro-2H—thiopyran-3-yl | ethyl | H | ethyl | |
| 233 | 5,6-dihydro-2H—thiopyran-3-yl | ethyl | H | allyl | |
| 234 | 5,6-dihydro-2H—thiopyran-3-yl | ethyl | H | (E)—3-chloroallyl | |
| 235 | 5,6-dihydro-2H—thiopyran-3-yl | ethyl | H | (E)—2-butenyl | |
| 236 | 5,6-dihydro-2H—thiopyran-3-yl | ethyl | H | 5-chlorothien-2-ylmethyl | |
| 237 | 5,6-dihydro-2H—thiopyran-3-yl | propyl | H | ethyl | |
| 238 | 5,6-dihydro-2H—thiopyran-3-yl | propyl | H | allyl | |
| 239 | 5,6-dihydro-2H—thiopyran-3-yl | propyl | H | (E)—3-chloroallyl | |

TABLE 2-continued $$\underset{R^3}{\overset{OR^1}{\underset{S}{\bigwedge}}}\overset{NO-R^4}{\underset{O}{\bigvee}}R^2 \quad (Ib)$$

| No. | R³ | R² | R¹ | R⁴ | Phys. data |
|---|---|---|---|---|---|
| 240 | 5,6-dihydro-2H—thiopyran-3-yl | propyl | H | (E)—2-butenyl | |
| 241 | 5,6-dihydro-2H—thiopyran-3-yl | propyl | H | 5-chlorothien-2-ylmethyl | |
| 242 | 2-isopropyl-1,3-dioxepan-5-yl | ethyl | H | ethyl | |
| 243 | 2-isopropyl-1,3-dioxepan-5-yl | ethyl | H | allyl | |
| 244 | 2-isopropyl-1,3-dioxepan-5-yl | ethyl | H | (E)—3-chloroallyl | |
| 245 | 2-isopropyl-1,3-dioxepan-5-yl | ethyl | H | (E)—2-butenyl | |
| 246 | 2-isopropyl-1,3-dioxepan-5-yl | ethyl | H | p-fluorophenylmethyl | |
| 247 | 2-isopropyl-1,3-dioxepan-5-yl | propyl | H | ethyl | |
| 248 | 2-isopropyl-1,3-dioxepan-5-yl | propyl | H | allyl | |
| 249 | 2-isopropyl-1,3-dioxepan-5-yl | propyl | H | (E)—3-chloroallyl | |
| 250 | 2-isopropyl-1,3-dioxepan-5-yl | propyl | H | (E)—2-butenyl | |
| 251 | 2-isopropyl-1,3-dioxepan-5-yl | propyl | H | p-fluorophenylmethyl | |
| 252 | 2-methyl-1,3-dioxepan-5-yl | ethyl | H | ethyl | |
| 253 | 2-methyl-1,3-dioxepan-5-yl | ethyl | H | allyl | |
| 254 | 2-methyl-1,3-dioxepan-5-yl | ethyl | H | (E)—3-chloroallyl | |
| 255 | 2-methyl-1,3-dioxepan-5-yl | ethyl | H | (E)—2-butenyl | |
| 256 | 2-methyl-1,3-dioxepan-5-yl | ethyl | H | p-nitrophenylmethyl | |
| 257 | 2-methyl-1,3-dioxepan-5-yl | propyl | H | ethyl | |
| 258 | 2-methyl-1,3-dioxepan-5-yl | propyl | H | allyl | |
| 259 | 2-methyl-1,3-dioxepan-5-yl | propyl | H | (E)—3-chloroallyl | |
| 260 | 2-methyl-1,3-dioxepan-5-yl | propyl | H | (E)—2-butenyl | |
| 261 | 2-methyl-1,3-dioxepan-5-yl | propyl | H | p-nitrophenylmethyl | |
| 262 | tetrahydrofuran-3-yl | ethyl | H | ethyl | |
| 263 | tetrahydrofuran-3-yl | ethyl | H | allyl | |
| 264 | tetrahydrofuran-3-yl | ethyl | H | (E)—3-chloroallyl | |
| 265 | tetrahydrofuran-3-yl | ethyl | H | (E)—2-butenyl | |
| 266 | tetrahydrofuran-3-yl | ethyl | H | 5-chlorothien-2-ylmethyl | |
| 267 | tetrahydrofuran-3-yl | propyl | H | ethyl | |
| 268 | tetrahydrofuran-3-yl | propyl | H | allyl | |
| 269 | tetrahydrofuran-3-yl | propyl | H | (E)—3-chloroallyl | |
| 270 | tetrahydrofuran-3-yl | propyl | H | (E)—2-butenyl | |
| 271 | tetrahydrofuran-3-yl | propyl | H | 5-chlorthien-2-ylmethyl | |
| 272 | tetrahydrofuran-2-yl | ethyl | H | ethyl | |
| 273 | tetrahydrofuran-2-yl | ethyl | H | allyl | |
| 274 | tetrahydrofuran-2-yl | ethyl | H | (E)—3-chloroallyl | |
| 275 | tetrahydrofuran-2-yl | ethyl | H | (E)—2-butenyl | |
| 276 | tetrahydrofuran-2-yl | ethyl | H | m-trifluoromethylphenylmethyl | |
| 277 | tetrahydrofuran-2-yl | propyl | H | ethyl | |
| 278 | tetrahydrofuran-2-yl | propyl | H | allyl | |
| 279 | tetrahydrofuran-2-yl | propyl | H | (E)—3-chloroallyl | |
| 280 | tetrahydrofuran-2-yl | propyl | H | (E)—2-butenyl | |
| 281 | tetrahydrofuran-2-yl | propyl | H | m-trifluoromethylphenylmethyl | |
| 282 | 5,6-dihydro-2,6-dimethyl-2H—pyran-3-yl | ethyl | H | ethyl | |
| 283 | 5,6-dihydro-2,6-dimethyl-2H—pyran-3-yl | ethyl | H | allyl | |
| 284 | 5,6-dihydro-2,6-dimethyl-2H—pyran-3-yl | ethyl | H | (E)—3-chloroallyl | |
| 285 | 5,6-dihydro-2,6-dimethyl-2H—pyran-3-yl | ethyl | H | (E)—2-butenyl | |
| 286 | 5,6-dihydro-2,6-dimethyl-2H—pyran-3-yl | ethyl | H | p-fluorophenylmethyl | |
| 287 | 5,6-dihydro-2,6-dimethyl-2H—pyran-3-yl | propyl | H | ethyl | |
| 288 | 5,6-dihydro-2,6-dimethyl-2H—pyran-3-yl | propyl | H | allyl | |
| 289 | 5,6-dihydro-2,6-dimethyl-2H—pyran-3-yl | propyl | H | (E)—3-chloroallyl | |
| 290 | 5,6-dihydro-2,6-dimethyl-2H—pyran-3-yl | propyl | H | (E)—2-butenyl | |
| 291 | 5,6-dihydro-2,6-dimethyl-2H—pyran-3-yl | propyl | H | p-fluorophenylmethyl | |
| 292 | 1,4-dioxanyl | ethyl | H | ethyl | |
| 293 | 1,4-dioxanyl | ethyl | H | allyl | |
| 294 | 1,4-dioxanyl | ethyl | H | (E)—3-chloroallyl | |
| 295 | 1,4-dioxanyl | ethyl | H | (E)—2-butenyl | |
| 296 | 1,4-dioxanyl | ethyl | H | p-nitrophenylmethyl | |
| 297 | 1,4-dioxanyl | propyl | H | ethyl | |
| 298 | 1,4-dioxanyl | propyl | H | allyl | |
| 299 | 1,4-dioxanyl | propyl | H | (E)—3-chloroallyl | |
| 300 | 1,4-dioxanyl | propyl | H | (E)—2-butenyl | |
| 301 | 1,4-dioxanyl | propyl | H | p-nitrophenylmethyl | |

TABLE 3

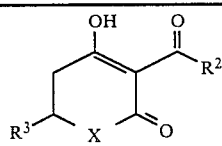

(Ic)

| No. | R³ | R² | X | Phys. data |
|---|---|---|---|---|
| 302 | tetrahydropyran-3-yl | ethyl | O | |
| 303 | tetrahydropyran-3-yl | ethyl | S | |
| 304 | tetrahydropyran-3-yl | propyl | O | NMR: 4.1–4.4 m; 3.8–4.0 m; 2.95–3.1 q, 0.9–1.1 t |
| 305 | tetrahydropyran-3-yl | propyl | S | |
| 306 | tetrahydropyran-3-yl | pentyl | O | |
| 307 | tetrahydrothiopyran-3-yl | ethyl | O | mp. 78–79° C. |
| 308 | tetrahydrothiopyran-3-yl | ethyl | S | |
| 309 | tetrahydrothiopyran-3-yl | propyl | O | NMR: 4.2–4.3 m; 2.9–3.0 q, 0.9–1.0 t |
| 310 | tetrahydrothiopyran-3-yl | propyl | S | |
| 311 | tetrahydrothiopyran-3-yl | pentyl | O | |
| 312 | tetrahydropyran-4-yl | ethyl | O | NMR: 1.22, m; 1.82–2.07, m; 2.88–3.28, m; 3.29–3.57, m; 3.9–4.4, m; |
| 313 | tetrahydropyran-4-yl | ethyl | S | |
| 314 | tetrahydropyran-4-yl | propyl | O | |
| 315 | tetrahydropyran-4-yl | propyl | S | |
| 316 | tetrahydrothiopyran-4-yl | ethyl | O | |
| 317 | tetrahydrothiopyran-4-yl | propyl | O | |
| 318 | 5,6-dihydro-2H—pyran-3-yl | ethyl | O | NMR: 1.2, m; 2.83–3.28, m; 4.7–4.92, m; 5.85–6.06, m; |
| 319 | 5,6-dihydro-2H—pyran-3-yl | ethyl | S | |
| 320 | 5,6-dihydro-2H—pyran-3-yl | propyl | O | |
| 321 | 5,6-dihydro-2H—pyran-3-yl | propyl | S | |
| 322 | 5,6-dihydro-2H—thiopyran-3-yl | ethyl | O | |
| 323 | 5,6-dihydro-2H—thiopyran-3-yl | ethyl | S | |
| 324 | 5,6-dihydro-2H—thiopyran-3-yl | propyl | O | |
| 325 | 5,6-dihydro-2H—thiopyran-3-yl | propyl | S | |
| 326 | 5,6-dihydro-2,6-dimethyl-2H—pyran-3-yl | ethyl | O | |
| 327 | 5,6-dihydro-2,6-dimethyl-2H—pyran-3-yl | ethyl | S | |
| 328 | 5,6-dihydro-2,6-dimethyl-2H—pyran-3-yl | propyl | O | |
| 329 | 5,6-dihydro-2,6-dimethyl-2H—pyran-3-yl | propyl | S | |
| 330 | 1,4-dioxanyl | ethyl | O | |
| 331 | 1,4-dioxanyl | ethyl | S | |
| 332 | 1,4-dioxanyl | propyl | O | |
| 333 | 1,4-dioxanyl | propyl | S | |
| 334 | tetrahydrofuran-2-yl | ethyl | O | |
| 335 | tetrahydrofuran-2-yl | ethyl | S | |
| 336 | tetrahydrofuran-2-yl | propyl | O | |
| 337 | tetrahydrofuran-2-yl | propyl | S | |
| 338 | tetrahydrofuran-3-yl | ethyl | O | |
| 339 | tetrahydrofuran-3-yl | ethyl | S | |
| 340 | tetrahydrofuran-3-yl | propyl | O | |
| 341 | tetrahydrofuran-3-yl | propyl | S | |
| 342 | 2-isopropyl-1,3-dioxepan-5-yl | ethyl | O | |
| 343 | 2-isopropyl-1,3-dioxepan-5-yl | ethyl | S | |
| 344 | 2-isopropyl-1,3-dioxepan-5-yl | propyl | O | |
| 345 | 2-isopropyl-1,3-dioxepan-5-yl | propyl | S | |
| 346 | 2-methyl-1,3-dioxepan-5-yl | ethyl | O | |
| 347 | 2-methyl-1,3-dioxepan-5-yl | ethyl | S | |
| 348 | 2-methyl-1,3-dioxepan-5-yl | propyl | O | |
| 349 | 2-methyl-1,3-dioxepan-5-yl | propyl | S | |

The tetrahydro(thio)pyran derivatives of the formula I, or herbicidal agents containing them, are tolerated by, and are thus selective in, broadleaved crops and monocotyledonous plants not belonging to the Gramineae. Some of the compounds are also selective in graminaceous crops such as wheat and rice, and combat unwanted grasses.

The compounds of the formula I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates. alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 51 is mixed with 10 parts by weight of N-methyl-alpha-pyrrolidone. A mixture is obtained which is suitable for application in the form of very fine drops.

II. 20 parts by weight of compound no. 52 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 36 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 53 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 54 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 71 is intimately mixed with 97 parts by weight of particulate kaolin. A dust is obtained containing 3% by weight of the active ingredient.

VII. 30 parts by weight of compound no. 36 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 51 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or herbicidal agents containing them, may be applied pre- or (preferably) postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amounts of active ingredient applied depend on the time of the year, the plants to be combated and their growth stage, and vary from 0.01 to 3, and preferably from 0.03 to 1, kg/ha.

In view of the spectrum of weeds that can be combined, the tolerance of the active ingredients by crop plants, and in view of the numerous application methods available, the compounds of the formula I, and herbicidal agents containing them, may be used in a large number of crops. The following may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |

-continued

| Botanical name | Common name |
| --- | --- |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotians tabacum (N. rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the tetrahydro(thio)pyran derivatives of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, sulfonylureas, imidazolinones, aryloxyphenoxypropionic acid derivatives, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Use examples

The action of the tetrahydro(thio)pyran derivatives of the formula I is demonstrated in greenhouse experiments:

The vessels employed were plastic flowerpots having a volume of 300 cm$^3$. A sandy loam containing about 3% humus was used as substrate. Peat was added to the soybean plants to give a better stand. The seeds of the test plants were sown shallow, and separately according to species.

For the preemergence treatment, the formulated active ingredients were applied to the surface of the soil immediately after the seeds had been sown. The compounds were emulsified or suspended in water as vehicle, and sprayed through finely distributing nozzles. The application rate was 3.0 kg/ha. After the agents had been applied, the vessels were lightly sprinkler irrigated to induce germination and growth. Transparent plastic covers were then placed on the vessels until the plants had taken root. The cover ensured uniform germination of the plants, insofar as this was not impaired by the active ingredients. For the postemergence treatment, the plants were grown, depending on growht form, to a height of from 3 to 15 cm before being treated. Either plants which had been sown directly in the pots and grown there were selected, or plants which had been grown from seedlings and transplanted to the vessels a few days before treatment. The application rates for postemergence treatment were 0.125 and 0.03 kg/ha.

The pots were set up in the greenhouse—species from warmer areas at from 20° to 35° C., and species from moderate climates at 10° to 25° C. The experiments were run for 2 to 4 weeks. During this period the plants were tended and their reactions to the various treatments assessed. The scale employed was 0 to 100, 100 denoting nonemergence or complete destruction of at least the visible plant parts, and 0 denoting no damage or normal emergence.

The influence of the treatment is assessed visually against the untreated control.

The plants used in the greenhouse experiments were Avena fatua, Avena sativa, Alopecurus myosuroides, Bromus inermis, Digitaria sanguinalis, Echinochloa crusgalli, Glycine max., Lolium multiflorum, Medicago sativa, Setaria italica, Sorghum halepense, and Zea mays.

Compound no. 38 selected by way of example had, when applied preemergence at a rate of 3.0 kg/ha, a good herbicidal action on grassy plants. When compound no. 38 was applied postemergence, small amounts were sufficient to combat unwanted plants from the Gramineae family. The crop plant alfalfa remained undamaged.

Active ingredient no. 51, applied postemergence at a rate of 0.125 kg/ha, was suitable for combating a broad spectrum of grassy plants. Soybeans, as an example of a broadleaved crop, remained completely uninfluenced.

Active ingredients nos. 36, 37, 51, 52, 53 and 54 had, on postemergence application, a strong herbicidal action on a broad spectrum of unwanted plants from the Gramineae family, whereas alfalfa, as an example of a broadleaved crop, remained completely undamaged.

Active ingredients nos. 36 and 71 had, when applied postemergence, a better action on unwanted grassy plants than active ingredients nos. 1 and 3 mentioned in Table 1 of GB-A-2 140 803.

We claim:

1. A tetrahydropyran-2,4-dione of the formula

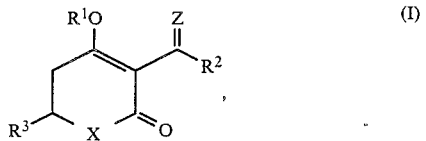

(I)

where $R^1$ is hydrogen, $C_1$–$C_{10}$-alkylcarbonyl, $C_2$–$C_{10}$-alkenylcarbonyl, or benzoyl which is unsubstituted or substituted in the phenyl ring by $C_1$–$C_8$-alkyl, $R^2$ is $C_1$–$C_5$-alkyl, $R^3$ is a non-aromatic, unsubstituted or $C_1$–$C_3$-alkyl-substituted, tetrahydropyranyl, tetrahydrothiopyranyl, 5,6-dihydro-2H-pyranyl, 5,6-dihydro-2H-thiopyranyl, tetrahydrofuranyl or 1,3-dioxepanyl, X is oxygen and Z is oxygen or the radical NO—$R^4$, $R^4$ denoting $C_1$–$C_4$-alkyl, $C_3$–$C_4$-alkenyl, $C_3$–$C_4$-alkynyl, $C_2$–$C_4$-haloalkyl, $C_2$–$C_4$-haloalkenyl, $C_2$–$C_3$-alkoxyalkyl or the radical $CH_2$—$R^5$, where $R^5$ is thienyl optionally bearing up to 2 halogen substituents and their agriculturally useful salts.

2. A tetrahydropyran-2,4-dione of the formula I as set forth in claim 1, where $R^2$ in formula I is $C_2$–$C_3$-alkyl.

3. A tetrahydropyran-2,4-dione of the formula I as set forth in claim 1, where $R^3$ is a non-aromatic 6-membered heterocyclic compound which is unsubstituted or substituted by $C_1$–$C_3$-alkyl.

4. A tetrahydropyran-2,4-dione of the formula I as set forth in calim 1, where $R^3$ is tetrahydropyranyl or tetrahydrothiopyranyl.

5. A tetrahydropyran-2,4-dione of the formula I as set forth in claim 1, where $R^1$ is hydrogen, $R^2$ is n-propyl, $R^3$ is tetrahydrothiopyran-3-yl and Z is NO—$R^4$, $R^4$ denoting ethyl.

6. A herbicidal composition containing inert additives and an effective amount of a tetrahydropyran-2,4-dione of the formula I as set forth in claim 1.

7. A process for combating the growth of unwanted plants, wherein the unwanted plants and/or the area to be kept free from unwanted plant growth are treated with a herbicidally effective amount of a tetrahydropyran-2,4-dione derivative of the formula I as set forth in claim 1, 2 denoting NO—$R^4$.

* * * * *